United States Patent
Spence et al.

(10) Patent No.: US 11,974,914 B2
(45) Date of Patent: *May 7, 2024

(54) DEVICES, SYSTEMS AND METHODS FOR DELIVERING A PROSTHETIC MITRAL VALVE AND ANCHORING DEVICE

(71) Applicant: Mitral Valve Technologies Sarl, Nyon (CH)

(72) Inventors: Paul A Spence, Louisville, KY (US); Landon H. Tompkins, Peachtree Corners, GA (US)

(73) Assignee: Mitral Valve Technologies Sarl, Nyon (CH)

( * ) Notice: Subject to any disclaimer, the term of this patent is extended or adjusted under 35 U.S.C. 154(b) by 638 days.

This patent is subject to a terminal disclaimer.

(21) Appl. No.: 17/156,265

(22) Filed: Jan. 22, 2021

(65) Prior Publication Data
US 2021/0137678 A1    May 13, 2021

Related U.S. Application Data

(63) Continuation of application No. 16/057,192, filed on Aug. 7, 2018, now Pat. No. 10,898,320, which is a
(Continued)

(51) Int. Cl.
*A61F 2/24* (2006.01)

(52) U.S. Cl.
CPC .......... *A61F 2/2418* (2013.01); *A61F 2/2412* (2013.01); *A61F 2/2427* (2013.01);
(Continued)

(58) Field of Classification Search
CPC .... A61F 2/2418; A61F 2/2412; A61F 2/2427; A61F 2/2436; A61F 2230/0069; A61F 2230/0091; A61F 2250/006
See application file for complete search history.

(56) References Cited

U.S. PATENT DOCUMENTS

| | | |
|---|---|---|
| 3,564,617 A | 2/1971 | Sauvage et al. |
| 3,755,823 A | 9/1973 | Hancock |

(Continued)

FOREIGN PATENT DOCUMENTS

| | | |
|---|---|---|
| CN | 1684644 A | 10/2005 |
| CN | 1714766 A | 1/2006 |

(Continued)

OTHER PUBLICATIONS

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

(Continued)

*Primary Examiner* — Ashley L Fishback
*Assistant Examiner* — Chima U Igboko
(74) *Attorney, Agent, or Firm* — Linda Allyson Nassif

(57) ABSTRACT

Prosthetic heart valves and anchors for use with such valves are provided that allow for an improved implantation procedure. In various embodiments, an anchoring device is formed as a coiled or twisted anchor that includes one or more turns that twist or curve around a central axis. One or more arms attached to the frame of the valve guide the anchoring device into position at the native valve as it exits the delivery catheter, and the expandable prosthetic valve is held within the coil of the anchoring device. The anchoring device and the valve can be delivered together, simplifying the valve replacement procedure.

12 Claims, 9 Drawing Sheets

Related U.S. Application Data continuation of application No. 14/628,060, filed on Feb. 20, 2015, now Pat. No. 10,052,199.

(60) Provisional application No. 61/943,125, filed on Feb. 21, 2014.

(52) U.S. Cl.
CPC .... *A61F 2/2436* (2013.01); *A61F 2230/0069* (2013.01); *A61F 2230/0091* (2013.01); *A61F 2250/006* (2013.01)

(56) References Cited

U.S. PATENT DOCUMENTS

| | | |
|---|---|---|
| 4,035,849 A | 7/1977 | Angell et al. |
| 4,490,859 A | 1/1985 | Black et al. |
| 4,512,338 A | 4/1985 | Balko et al. |
| 4,759,758 A | 7/1988 | Gabbay |
| 4,777,951 A | 10/1988 | Cribier et al. |
| 4,787,899 A | 11/1988 | Lazarus |
| 4,790,843 A | 12/1988 | Carpentier et al. |
| 4,796,629 A | 1/1989 | Grayzel |
| 4,856,516 A | 8/1989 | Hillstead |
| 4,878,495 A | 11/1989 | Grayzel |
| 4,966,604 A | 10/1990 | Reiss |
| 4,994,077 A | 2/1991 | Dobben |
| 5,059,177 A | 10/1991 | Towne et al. |
| 5,192,297 A | 3/1993 | Hull |
| 5,282,847 A | 2/1994 | Trescony et al. |
| 5,370,685 A | 12/1994 | Stevens |
| 5,403,305 A | 4/1995 | Sauter et al. |
| 5,411,552 A | 5/1995 | Andersen et al. |
| 5,443,500 A | 8/1995 | Sigwart |
| 5,545,214 A | 8/1996 | Stevens |
| 5,554,185 A | 9/1996 | Block et al. |
| 5,558,644 A | 9/1996 | Boyd et al. |
| 5,584,803 A | 12/1996 | Stevens et al. |
| 5,591,195 A | 1/1997 | Taheri et al. |
| 5,607,464 A | 3/1997 | Trescony et al. |
| 5,665,115 A | 9/1997 | Cragg |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,925,063 A | 7/1999 | Khosravi |
| 5,957,949 A | 9/1999 | Leonhardt et al. |
| 6,027,525 A | 2/2000 | Suh et al. |
| 6,120,534 A | 9/2000 | Ruiz |
| 6,168,614 B1 | 1/2001 | Andersen et al. |
| 6,221,091 B1 | 4/2001 | Khosravi |
| 6,235,042 B1 | 5/2001 | Katzman |
| 6,245,102 B1 | 6/2001 | Jayaraman |
| 6,302,906 B1 | 10/2001 | Goicoechea et al. |
| 6,306,141 B1 | 10/2001 | Jervis |
| 6,406,492 B1 | 6/2002 | Lytle |
| 6,409,758 B2 | 6/2002 | Stobie et al. |
| 6,419,696 B1 | 7/2002 | Ortiz et al. |
| 6,425,916 B1 | 7/2002 | Garrison et al. |
| 6,432,134 B1 | 8/2002 | Anson et al. |
| 6,454,799 B1 | 9/2002 | Schreck |
| 6,458,153 B1 | 10/2002 | Bailey et al. |
| 6,461,382 B1 | 10/2002 | Cao |
| 6,482,228 B1 | 11/2002 | Norred |
| 6,527,979 B2 | 3/2003 | Constantz |
| 6,582,462 B1 | 6/2003 | Andersen et al. |
| 6,625,578 B2 | 9/2003 | Spaur et al. |
| 6,652,578 B2 | 11/2003 | Bailey et al. |
| 6,730,118 B2 | 5/2004 | Spenser et al. |
| 6,730,121 B2 | 5/2004 | Ortiz et al. |
| 6,733,525 B2 | 5/2004 | Yang et al. |
| 6,767,362 B2 | 7/2004 | Schreck |
| 6,797,002 B2 | 9/2004 | Spence et al. |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 6,971,998 B2 | 12/2005 | Rosenman et al. |
| 7,018,406 B2 | 3/2006 | Seguin et al. |
| 7,018,408 B2 | 3/2006 | Bailey et al. |
| 7,037,334 B1 | 5/2006 | Hlavka et al. |
| 7,077,861 B2 | 7/2006 | Spence |
| 7,101,395 B2 | 9/2006 | Tremulis et al. |
| 7,125,421 B2 | 10/2006 | Tremulis et al. |
| 7,166,126 B2 | 1/2007 | Spence et al. |
| 7,166,127 B2 | 1/2007 | Spence et al. |
| 7,276,078 B2 | 10/2007 | Spenser et al. |
| 7,276,084 B2 | 10/2007 | Yang et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,404,824 B1 | 7/2008 | Webler et al. |
| 7,431,726 B2 | 10/2008 | Spence et al. |
| 7,445,632 B2 | 11/2008 | McGuckin, Jr. et al. |
| 7,462,191 B2 | 12/2008 | Spenser et al. |
| 7,510,575 B2 | 3/2009 | Spenser et al. |
| 7,527,646 B2 | 5/2009 | Rahdert et al. |
| 7,585,321 B2 | 9/2009 | Cribier |
| 7,618,446 B2 | 11/2009 | Andersen et al. |
| 7,618,449 B2 | 11/2009 | Tremulis et al. |
| 7,637,946 B2 | 12/2009 | Solem et al. |
| 7,655,034 B2 | 2/2010 | Mitchell et al. |
| 7,708,775 B2 | 5/2010 | Rowe et al. |
| 7,737,060 B2 | 6/2010 | Strickler et al. |
| 7,758,639 B2 | 7/2010 | Mathis |
| 7,780,726 B2 | 8/2010 | Seguin |
| 7,785,366 B2 | 8/2010 | Maurer et al. |
| 7,942,927 B2 | 5/2011 | Kaye et al. |
| 7,951,195 B2 | 5/2011 | Antonsson et al. |
| 7,955,385 B2 | 6/2011 | Crittenden |
| 7,959,672 B2 | 6/2011 | Salahieh et al. |
| 7,967,857 B2 | 6/2011 | Lane |
| 7,993,394 B2 | 8/2011 | Hariton et al. |
| 8,016,882 B2 | 9/2011 | Macoviak et al. |
| 8,029,556 B2 | 10/2011 | Rowe |
| 8,052,750 B2 | 11/2011 | Tuval et al. |
| 8,092,520 B2 | 1/2012 | Quadri |
| 8,128,691 B2 | 3/2012 | Keranen |
| 8,142,492 B2 | 3/2012 | Forster et al. |
| 8,167,932 B2 | 5/2012 | Bourang et al. |
| 8,167,935 B2 | 5/2012 | McGuckin, Jr. et al. |
| 8,236,049 B2 | 8/2012 | Rowe et al. |
| 8,323,335 B2 | 12/2012 | Rowe et al. |
| 8,377,115 B2 | 2/2013 | Thompson |
| 8,398,708 B2 | 3/2013 | Meiri et al. |
| 8,449,599 B2 | 5/2013 | Chau et al. |
| 8,449,605 B2 | 5/2013 | Lichtenstein et al. |
| 8,449,606 B2 | 5/2013 | Eliasen et al. |
| 8,652,203 B2 | 2/2014 | Quadri et al. |
| 8,657,872 B2 | 2/2014 | Seguin |
| 8,663,322 B2 | 3/2014 | Keranen |
| 8,672,998 B2 | 3/2014 | Lichtenstein et al. |
| 8,685,086 B2 | 4/2014 | Navia et al. |
| 8,734,507 B2 | 5/2014 | Keranen |
| 8,795,352 B2 | 8/2014 | O'Beirne et al. |
| 8,801,776 B2 | 8/2014 | House et al. |
| 8,840,664 B2 | 9/2014 | Karapetian et al. |
| 8,986,373 B2 | 3/2015 | Chau et al. |
| 9,078,747 B2 | 7/2015 | Conklin |
| 9,095,434 B2 | 8/2015 | Rowe |
| 9,119,718 B2 | 9/2015 | Keranen |
| 9,180,006 B2 | 11/2015 | Keranen |
| 9,192,471 B2 | 11/2015 | Bolling |
| 9,237,886 B2 | 1/2016 | Seguin et al. |
| 9,314,335 B2 | 4/2016 | Konno |
| 9,326,853 B2 | 5/2016 | Olson et al. |
| 9,364,326 B2 | 6/2016 | Yaron |
| 9,463,268 B2 | 10/2016 | Spence |
| 9,474,599 B2 | 10/2016 | Keranen |
| 9,526,572 B2 | 12/2016 | Kunis |
| 9,597,205 B2 | 3/2017 | Tuval |
| 9,622,863 B2 | 4/2017 | Karapetian et al. |
| 9,700,409 B2 | 7/2017 | Braido et al. |

(56) References Cited

U.S. PATENT DOCUMENTS

| | | |
|---|---|---|
| 9,867,702 B2 | 1/2018 | Keränen et al. |
| 10,016,272 B2 | 7/2018 | Spence et al. |
| 10,016,276 B2 | 7/2018 | Brunnett et al. |
| 10,034,749 B2 | 7/2018 | Spence et al. |
| 10,039,637 B2 | 8/2018 | Maimon et al. |
| 10,052,198 B2 | 8/2018 | Chau et al. |
| 10,195,028 B2 | 2/2019 | Hosmer et al. |
| 10,195,033 B2 | 2/2019 | Tuval et al. |
| 10,226,339 B2 | 3/2019 | Spence et al. |
| 10,357,361 B2 | 7/2019 | Rafi et al. |
| 10,463,479 B2 | 11/2019 | Manash et al. |
| 10,828,150 B2 | 11/2020 | Tamir |
| 11,020,225 B2 | 6/2021 | Keränen et al. |
| 11,039,924 B2 | 6/2021 | Yaron |
| 11,065,111 B2 | 7/2021 | Manash et al. |
| 11,141,273 B2 | 10/2021 | Dakin et al. |
| 11,185,406 B2 | 11/2021 | Haivatov et al. |
| 11,364,114 B2 | 6/2022 | Gorman, III et al. |
| 11,382,748 B2 | 7/2022 | Keränen et al. |
| 11,471,282 B2 | 10/2022 | Argento et al. |
| 11,547,563 B2 | 1/2023 | Keränen et al. |
| 11,654,025 B2 | 5/2023 | O'Carroll et al. |
| 11,666,441 B2 | 6/2023 | McDaniel et al. |
| 2002/0026094 A1 | 2/2002 | Roth |
| 2002/0032481 A1 | 3/2002 | Gabbay |
| 2002/0045936 A1 | 4/2002 | Moe |
| 2002/0055773 A1 | 5/2002 | Campbell et al. |
| 2002/0107535 A1 | 8/2002 | Wei et al. |
| 2002/0138135 A1 | 9/2002 | Duerig et al. |
| 2002/0151970 A1 | 10/2002 | Garrison et al. |
| 2002/0173841 A1 | 11/2002 | Ortiz et al. |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0167089 A1 | 9/2003 | Lane |
| 2003/0212454 A1 | 11/2003 | Scott et al. |
| 2003/0225420 A1 | 12/2003 | Wardle |
| 2004/0111006 A1 | 6/2004 | Alferness et al. |
| 2004/0167620 A1 | 8/2004 | Ortiz et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0096736 A1 | 5/2005 | Osse et al. |
| 2005/0119682 A1 | 6/2005 | Nguyen et al. |
| 2005/0119735 A1 | 6/2005 | Spence et al. |
| 2005/0137691 A1 | 6/2005 | Salahieh et al. |
| 2005/0149178 A1 | 7/2005 | Spence |
| 2005/0182486 A1 | 8/2005 | Gabbay |
| 2005/0203614 A1 | 9/2005 | Forster et al. |
| 2005/0203617 A1 | 9/2005 | Forster et al. |
| 2005/0228496 A1 | 10/2005 | Mensah et al. |
| 2005/0234546 A1 | 10/2005 | Nugent et al. |
| 2006/0020327 A1 | 1/2006 | Lashinski et al. |
| 2006/0025857 A1 | 2/2006 | Bergheim et al. |
| 2006/0052867 A1 | 3/2006 | Revuelta et al. |
| 2006/0058872 A1 | 3/2006 | Salahieh et al. |
| 2006/0149350 A1 | 7/2006 | Patel et al. |
| 2006/0195134 A1 | 8/2006 | Crittenden |
| 2006/0195185 A1 | 8/2006 | Lane et al. |
| 2006/0265056 A1 | 11/2006 | Nguyen et al. |
| 2006/0271172 A1 | 11/2006 | Tehrani |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0112422 A1 | 5/2007 | Dehdashtian |
| 2007/0185572 A1 | 8/2007 | Solem et al. |
| 2007/0203503 A1 | 8/2007 | Salahieh et al. |
| 2007/0203575 A1 | 8/2007 | Forster et al. |
| 2007/0213813 A1 | 9/2007 | Von Segesser et al. |
| 2007/0232898 A1 | 10/2007 | Huynh et al. |
| 2007/0244553 A1 | 10/2007 | Rafiee et al. |
| 2007/0265700 A1 | 11/2007 | Eliasen et al. |
| 2007/0293808 A1 | 12/2007 | Williams et al. |
| 2008/0004697 A1 | 1/2008 | Lichtenstein et al. |
| 2008/0021547 A1 | 1/2008 | Davidson |
| 2008/0033542 A1 | 2/2008 | Antonsson et al. |
| 2008/0077235 A1 | 3/2008 | Kirson |
| 2008/0114442 A1 | 5/2008 | Mitchell et al. |
| 2008/0125853 A1 | 5/2008 | Bailey et al. |
| 2008/0140190 A1 | 6/2008 | Macoviak et al. |
| 2008/0200977 A1 | 8/2008 | Paul et al. |
| 2008/0200980 A1 | 8/2008 | Robin et al. |
| 2008/0208327 A1 | 8/2008 | Rowe |
| 2008/0208330 A1 | 8/2008 | Keranen |
| 2008/0228265 A1 | 9/2008 | Spence et al. |
| 2008/0243245 A1 | 10/2008 | Thambar et al. |
| 2008/0275503 A1 | 11/2008 | Spence et al. |
| 2009/0005863 A1 | 1/2009 | Goetz et al. |
| 2009/0088836 A1 | 4/2009 | Bishop et al. |
| 2009/0099653 A1 | 4/2009 | Suri et al. |
| 2009/0157175 A1 | 6/2009 | Benichou |
| 2009/0177278 A1 | 7/2009 | Spence |
| 2009/0192601 A1 | 7/2009 | Rafiee et al. |
| 2009/0234318 A1 | 9/2009 | Loulmet et al. |
| 2009/0259307 A1 | 10/2009 | Gross et al. |
| 2009/0276038 A1 | 11/2009 | Tremulis et al. |
| 2009/0276040 A1 | 11/2009 | Rowe et al. |
| 2009/0281619 A1 | 11/2009 | Le et al. |
| 2009/0299471 A1 | 12/2009 | Keranen |
| 2009/0319037 A1 | 12/2009 | Rowe et al. |
| 2010/0036484 A1 | 2/2010 | Hariton et al. |
| 2010/0049313 A1 | 2/2010 | Alon et al. |
| 2010/0076548 A1 | 3/2010 | Konno |
| 2010/0076549 A1 | 3/2010 | Keidar et al. |
| 2010/0145440 A1 | 6/2010 | Keranen |
| 2010/0152839 A1 | 6/2010 | Shandas et al. |
| 2010/0161047 A1 | 6/2010 | Cabiri |
| 2010/0168844 A1 | 7/2010 | Toomes et al. |
| 2010/0198347 A1 | 8/2010 | Zakay et al. |
| 2010/0217382 A1 | 8/2010 | Chau et al. |
| 2010/0217385 A1 | 8/2010 | Thompson et al. |
| 2010/0312333 A1 | 12/2010 | Navia et al. |
| 2010/0318183 A1 | 12/2010 | Keranen |
| 2010/0318184 A1 | 12/2010 | Spence |
| 2010/0331971 A1 | 12/2010 | Keranen et al. |
| 2010/0331973 A1 | 12/2010 | Keranen |
| 2011/0015729 A1 | 1/2011 | Jimenez et al. |
| 2011/0098802 A1 | 4/2011 | Braido et al. |
| 2011/0106247 A1 | 5/2011 | Miller et al. |
| 2011/0137397 A1 | 6/2011 | Chau et al. |
| 2011/0178597 A9 | 7/2011 | Navia et al. |
| 2011/0196480 A1 | 8/2011 | Cartledge |
| 2011/0208297 A1 | 8/2011 | Tuval et al. |
| 2011/0208298 A1 | 8/2011 | Tuval et al. |
| 2011/0218621 A1 | 9/2011 | Antonsson et al. |
| 2011/0224785 A1 | 9/2011 | Hacohen |
| 2011/0245911 A1* | 10/2011 | Quill ................ A61F 2/2436 623/2.11 |
| 2011/0288634 A1 | 11/2011 | Tuval et al. |
| 2011/0295361 A1 | 12/2011 | Claiborne, III et al. |
| 2011/0319989 A1 | 12/2011 | Lane et al. |
| 2011/0319990 A1 | 12/2011 | Macoviak et al. |
| 2012/0016464 A1 | 1/2012 | Seguin |
| 2012/0022629 A1 | 1/2012 | Perera et al. |
| 2012/0022633 A1 | 1/2012 | Olson et al. |
| 2012/0053680 A1 | 3/2012 | Bolling et al. |
| 2012/0059458 A1 | 3/2012 | Buchbinder et al. |
| 2012/0123529 A1 | 5/2012 | Levi et al. |
| 2012/0150287 A1 | 6/2012 | Forster et al. |
| 2012/0215236 A1 | 8/2012 | Matsunaga et al. |
| 2012/0259409 A1 | 10/2012 | Nguyen et al. |
| 2012/0283820 A1 | 11/2012 | Tseng et al. |
| 2012/0310328 A1 | 12/2012 | Olson et al. |
| 2012/0316643 A1 | 12/2012 | Keranen |
| 2012/0323316 A1 | 12/2012 | Chau et al. |
| 2013/0006352 A1 | 1/2013 | Yaron |
| 2013/0023985 A1 | 1/2013 | Khairkhahan et al. |
| 2013/0114214 A1 | 5/2013 | Takeguchi et al. |
| 2013/0190857 A1 | 7/2013 | Mitra et al. |
| 2013/0190865 A1 | 7/2013 | Anderson |
| 2013/0204311 A1 | 8/2013 | Kunis |
| 2013/0274873 A1 | 10/2013 | Delaloye et al. |
| 2013/0310917 A1 | 11/2013 | Richter et al. |

(56) References Cited

U.S. PATENT DOCUMENTS

| | | | |
|---|---|---|---|
| 2013/0310928 A1* | 11/2013 | Morriss | A61F 2/2409 623/2.18 |
| 2013/0317598 A1 | 11/2013 | Rowe et al. | |
| 2013/0325114 A1 | 12/2013 | McLean et al. | |
| 2013/0331929 A1 | 12/2013 | Mitra et al. | |
| 2014/0067054 A1 | 3/2014 | Chau et al. | |
| 2014/0074299 A1 | 3/2014 | Endou et al. | |
| 2014/0081394 A1 | 3/2014 | Keranen et al. | |
| 2014/0155997 A1 | 6/2014 | Braido | |
| 2014/0163669 A1 | 6/2014 | Ben-Zvi et al. | |
| 2014/0172070 A1 | 6/2014 | Seguin | |
| 2014/0194981 A1 | 7/2014 | Menk et al. | |
| 2014/0200661 A1 | 7/2014 | Pintor et al. | |
| 2014/0236287 A1 | 8/2014 | Clague et al. | |
| 2014/0277417 A1 | 9/2014 | Schraut et al. | |
| 2014/0277419 A1 | 9/2014 | Garde et al. | |
| 2014/0277424 A1 | 9/2014 | Oslund | |
| 2014/0330372 A1 | 11/2014 | Weston et al. | |
| 2014/0343671 A1 | 11/2014 | Yohanan et al. | |
| 2014/0350667 A1 | 11/2014 | Braido et al. | |
| 2014/0358222 A1 | 12/2014 | Gorman et al. | |
| 2014/0358224 A1 | 12/2014 | Tegels et al. | |
| 2014/0379074 A1* | 12/2014 | Spence | A61F 2/2409 623/2.11 |
| 2014/0379076 A1 | 12/2014 | Vidlund et al. | |
| 2015/0025623 A1 | 1/2015 | Granada et al. | |
| 2015/0073545 A1 | 3/2015 | Braido | |
| 2015/0073546 A1 | 3/2015 | Braido | |
| 2015/0190227 A1 | 7/2015 | Johnson et al. | |
| 2015/0230921 A1 | 8/2015 | Chau et al. | |
| 2015/0245910 A1 | 9/2015 | Righini et al. | |
| 2015/0282931 A1 | 10/2015 | Brunnett et al. | |
| 2015/0335428 A1 | 11/2015 | Keranen | |
| 2015/0335430 A1 | 11/2015 | Loulmet et al. | |
| 2015/0374493 A1 | 12/2015 | Yaron et al. | |
| 2016/0015514 A1 | 1/2016 | Lashinski et al. | |
| 2016/0074165 A1 | 3/2016 | Spence et al. | |
| 2016/0095705 A1 | 4/2016 | Keranen et al. | |
| 2016/0143732 A1 | 5/2016 | Glimsdale | |
| 2016/0184095 A1 | 6/2016 | Spence et al. | |
| 2016/0199177 A1 | 7/2016 | Spence et al. | |
| 2016/0256276 A1 | 9/2016 | Yaron | |
| 2016/0346080 A1 | 12/2016 | Righini et al. | |
| 2017/0007399 A1 | 1/2017 | Keranen | |
| 2017/0007402 A1 | 1/2017 | Zerkowski et al. | |
| 2017/0217385 A1 | 8/2017 | Rinkleff et al. | |
| 2017/0266005 A1 | 9/2017 | McGuckin, Jr. | |
| 2017/0273788 A1 | 9/2017 | O'Carroll et al. | |
| 2017/0273789 A1 | 9/2017 | Yaron et al. | |
| 2017/0281337 A1 | 10/2017 | Campbell | |
| 2017/0360426 A1 | 12/2017 | Hacohen et al. | |
| 2018/0000580 A1 | 1/2018 | Wallace et al. | |
| 2018/0085217 A1 | 3/2018 | Lashinski et al. | |
| 2018/0206074 A1 | 7/2018 | Tanasa et al. | |
| 2018/0289481 A1 | 10/2018 | Dolan | |
| 2018/0303606 A1 | 10/2018 | Rothstein et al. | |
| 2018/0318073 A1 | 11/2018 | Tseng et al. | |
| 2018/0318080 A1 | 11/2018 | Quill et al. | |
| 2020/0054453 A1 | 2/2020 | Zerkowski et al. | |
| 2020/0360143 A1 | 11/2020 | O'Carroll et al. | |
| 2021/0212826 A1 | 7/2021 | Zerkowski et al. | |
| 2021/0361426 A1 | 11/2021 | Hacohen | |
| 2023/0086853 A1 | 3/2023 | Zerkowski et al. | |

FOREIGN PATENT DOCUMENTS

| | | |
|---|---|---|
| CN | 101588771 A | 11/2009 |
| CN | 102670332 A | 9/2012 |
| DE | 19532846 A1 | 3/1997 |
| DE | 19546692 A1 | 6/1997 |
| DE | 19857887 A1 | 7/2000 |
| DE | 19907646 A1 | 8/2000 |
| EP | 0103546 A1 | 3/1984 |
| EP | 0597967 A1 | 5/1994 |
| EP | 0592410 B1 | 10/1995 |
| EP | 0850607 A1 | 7/1998 |
| EP | 1432369 A1 | 6/2004 |
| EP | 1521550 A2 | 4/2005 |
| EP | 1796597 A2 | 6/2007 |
| EP | 1296618 B1 | 1/2008 |
| EP | 2072027 A1 | 6/2009 |
| EP | 1827314 B1 | 12/2010 |
| EP | 2620125 A1 | 7/2013 |
| EP | 2726018 A2 | 5/2014 |
| EP | 2806829 A2 | 12/2014 |
| EP | 3395296 B1 | 12/2019 |
| EP | 2747708 B1 | 1/2022 |
| FR | 2788217 A1 | 7/2000 |
| FR | 2815844 A1 | 5/2002 |
| JP | 2004502494 A | 1/2004 |
| JP | 2008531185 A | 8/2008 |
| SU | 1271508 A1 | 11/1986 |
| WO | 9117720 A1 | 11/1991 |
| WO | 9301768 A1 | 2/1993 |
| WO | 9829057 A1 | 7/1998 |
| WO | 9940964 A1 | 8/1999 |
| WO | 9947075 A1 | 9/1999 |
| WO | 0041652 A1 | 7/2000 |
| WO | 0047139 A1 | 8/2000 |
| WO | 0149213 A2 | 7/2001 |
| WO | 0154625 A1 | 8/2001 |
| WO | 0162189 A1 | 8/2001 |
| WO | 0164137 A1 | 9/2001 |
| WO | 0176510 A2 | 10/2001 |
| WO | 0203892 A1 | 1/2002 |
| WO | 0222054 A1 | 3/2002 |
| WO | 0236048 A1 | 5/2002 |
| WO | 0247575 A2 | 6/2002 |
| WO | 03028558 A2 | 4/2003 |
| WO | 03047468 A1 | 6/2003 |
| WO | 2005034812 A1 | 4/2005 |
| WO | 2005084595 A1 | 9/2005 |
| WO | 2006011127 A2 | 2/2006 |
| WO | 2006091163 A1 | 8/2006 |
| WO | 2006111391 A1 | 10/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008015257 A2 | 2/2008 |
| WO | 2008058940 A1 | 5/2008 |
| WO | 2008091515 A2 | 7/2008 |
| WO | 2009033469 A1 | 3/2009 |
| WO | 2009080801 A1 | 7/2009 |
| WO | 2009134701 A2 | 11/2009 |
| WO | 2009155561 A2 | 12/2009 |
| WO | 2010057262 A1 | 5/2010 |
| WO | 2010121076 A2 | 10/2010 |
| WO | 2012063228 A1 | 5/2012 |
| WO | 2013001339 A2 | 1/2013 |
| WO | 2013068542 A1 | 5/2013 |
| WO | 2013110722 A2 | 8/2013 |
| WO | 2013114214 A2 | 8/2013 |
| WO | 2015023579 A1 | 2/2015 |
| WO | 2015023862 A2 | 2/2015 |
| WO | 2015125024 A2 | 8/2015 |
| WO | 2015127264 A1 | 8/2015 |
| WO | 2015198125 A1 | 12/2015 |
| WO | 2016038017 A1 | 3/2016 |
| WO | 2016040881 A1 | 3/2016 |
| WO | 2016130820 A1 | 8/2016 |
| WO | 2017103833 A1 | 6/2017 |

OTHER PUBLICATIONS

Andersen, H.R. "History of Percutaneous Aortic Valve Prosthesis," Herz No. 34. pp. 343-346. 2009.

Andersen, H.R., et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.

(56) References Cited

OTHER PUBLICATIONS

Bailey, S. "Percutaneous Expandable Prosthetic Valves," Textbook of Interventional Cardiology vol. 2, 2nd Ed. pp. 1268-1276. 1994.
Bonhoeffer et at., "Percutaneous Replacement of Pulmonary valve in a Right-Ventricle to Pulmonary-Artery Prosthetic Conduit with Valve Dysfunction," Early Report, The Lancet, vol. 356, Oct. 21, 2000.
Casselman et al., "Reducing Operative Morality in Valvular Reoperations: The "valve in ring" Procedure," Brief Technique Reports, The Journal of Thoracic and Cardiovascular Surgery, vol. 141, No. 5. May 2011.
Cheung et al, Live Case Transmissions, NYHA III CHF, Case Summary, Sep. 23, 2010, St. Paul's Hospital/ University of British Columbia.
Cheung et al, "Transapical Transcatheter Mitral Valve-in-Valve Implantation in a Human," The Society of Thoracic Surgeons, 2009.
Descoutures et al., "Transcatheter Valve-in-Ring Implantation After Failure of Surgical Mitral Repair," European Journal of Cardio-Thoracic Surgery 44, e8-e15, 2013.
Himbert et al., "Transseptal Implantation of a Transcatheter Heart Valve in a Mitral Annuloplasty Ring to Treat Mitral Repair Failure," Circulation Cardiovascular Interventions, American Heart Association, 2011.
Himbert, Dominique, "Transvenous Mitral Valve Repair Replacement After Failure of Surgical Ring Annuloplasty," Research Correspondence, Journal of the American College of Cardiology, 2012.
International Search Report from corresponding PCT case No. PCT/IB2015/000901 dated Feb. 15, 2015.
Kempfert et al., "Minimally invasive off-pump valve-in-a-ring implantation: the atrial transcatheter approach for re-operative mitral valve replacement after failed repair," European Journal of Cardiothoracic Surgery, 2009, 35:965-969.
Ma et al., "Double-Crowned Valved Stents for Off-Pump Mitral Valve Replacement," European Journal of Cardio-Thoracic Surgery, 28, 194-199, 2005.
Pavcnik, et al. "Development and initial Experimental Evaluation of a Prosthetic Aortic Valve for Transcatheter Placement," Cardiovascular Radiology, vol. 183, No. 1. pp. 151-154. 1992.
Ross, "Aortic Valve Surgery," At a meeting of the Council on Aug. 4, 1966. pp. 192-197.
Sabbah, et al. "Mechanical Factors in the Degeneration of Porcine Bioprosthetic Valves: An Overview," Journal of Cardiac Surgery, vol. 4, No. 4. pp. 302-309. 1989.
Shuto et al., "Percutaneous Transvenous Melody Valve-in-Ring Procedure for Mitral Valve Replacement," J Am Coll Cardiol, 58(24): 2475-2480, 2011.
Uchida, "Modifications of Gianturco Expandable Wire Stents," American Journal of Roentgenology, vol. 150. pp. 1185-1187. 1986.
Walther et al., "Human Minimally Invasive Off-Pump Valve-in-a-Valve Implantation," Case Reports, The Society of Thoracic Surgeons, 2008.
Walther et al., "Valve-in-a-Valve Concept for Transcatheter Minimally Invasive Repeat Xenograph Implantation," Preclinical Studies, Journal of the American College of Cardiology, 2007.
Webb et al., "Mitral Valve in Valve," TCT Sep. 2009, Live Case: 30 Minutes, St. Paul's Hospital/University of British Columbia.
Webb et al., "Transcatheter Valve-in-Valve Implantation for Failed Bioprosthetic Heart Valves," Journal of the American Heart Association, 11, Apr. 27, 2010.
Weger et al., "First-in-Man Implantation of a Trans-Catheter Aortic Valve in a Mitral Annuloplasty Ring: Novel Treatment Modality for Failed Mitral Valve Repair," European Journal of Cardio-Thoracic Surgery 39, 1054-1056, 2011.
Wenaweser et al., "Percutaneous Aortic Valve Replacement for Severe Aortic Regurgitation in Degenerated Bioprosthesis: The First Valve Procedure Using Corevalve Revalving System," Catheterization and Cardiovascular Interventions, 70:760-764, 2007.
Wheatley, "Valve Prostheses," Operative Surgery, 4th ed. pp. 415-424. 1986.
Walther, et al., "Trans-catheter valve-in-valve implantation: in vitro hydrodynamic performance of the SAPIEN + cloth trans-catheter heart valve in the Carpentier-Edwards Perimount valves," European Journal of Cardio-thoracic Surgery, 40 (2011) 1120-1126, Sep. 23, 2010.

* cited by examiner

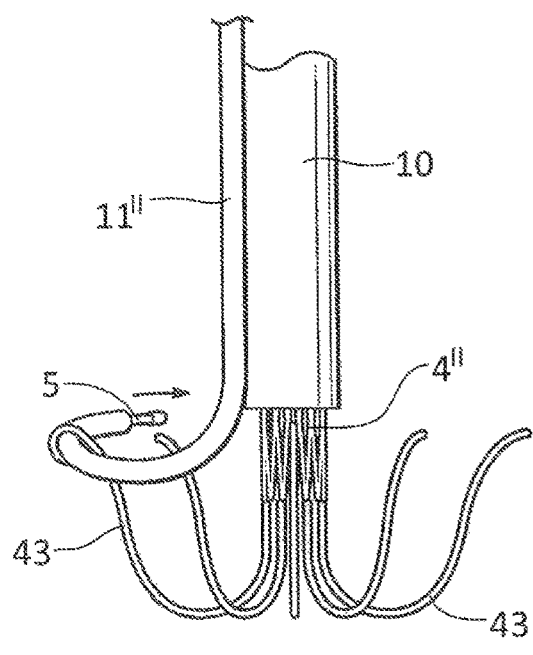
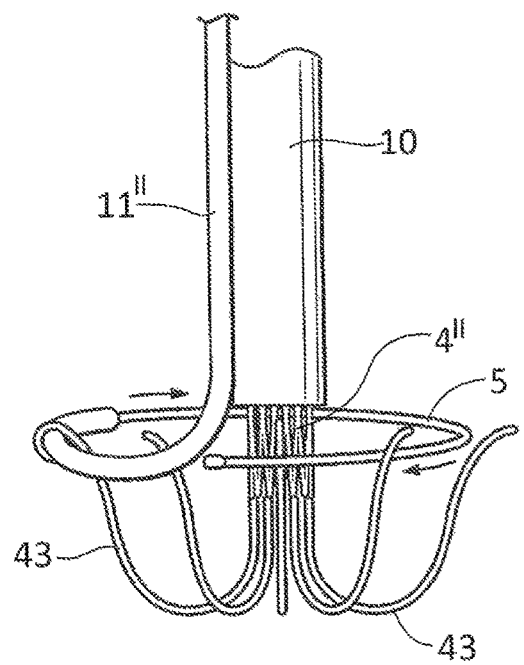
FIG.4A  FIG.4B
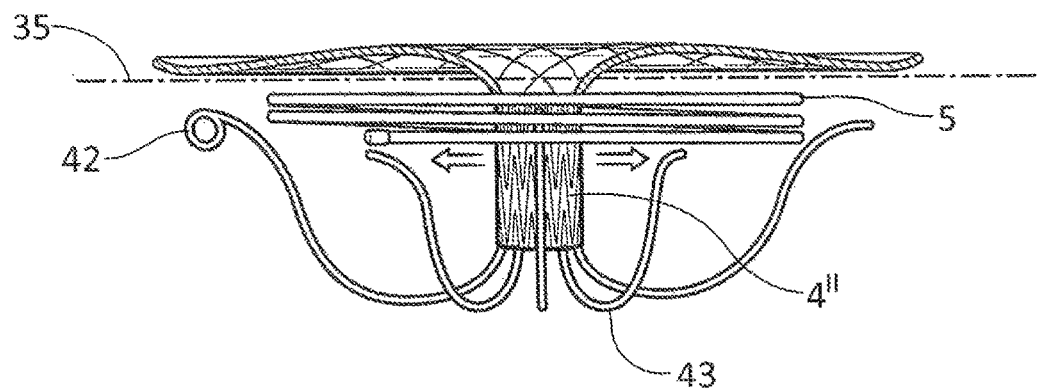
FIG.4C

DEVICES, SYSTEMS AND METHODS FOR DELIVERING A PROSTHETIC MITRAL VALVE AND ANCHORING DEVICE

CROSS-REFERENCE TO RELATED APPLICATION

The present disclosure is a continuation of U.S. patent application Ser. No. 16/057,192, filed Aug. 7, 2018, which is a continuation of U.S. patent application Ser. No. 14/628,060, filed Feb. 20, 2015, which claims the benefit of U.S. Provisional Patent Application Ser. No. 61/943,125, filed Feb. 21, 2014, the contents of each of the foregoing are incorporated by reference herein in their entirety.

BACKGROUND FIELD

Complications of the mitral valve, which controls the flow of blood from the left atrium into the left ventricle of the human heart, have been known to cause fatal heart failure. In the developed world, one of the most common forms of valvular heart disease is mitral valve leak, also known as mitral regurgitation, which is characterized by the abnormal leaking of blood from the left ventricle through the mitral valve and back into the left atrium. This occurs most commonly due to ischemic heart disease when the leaflets of the mitral valve no longer meet or close properly after multiple infarctions, idiopathic and hypertensive cardiomyopathies where the left ventricle enlarges, and with leaflet and chordal abnormalities, such as those caused by a degenerative disease.

In addition to mitral regurgitation, rheumatic disease can lead to mitral narrowing or stenosis. While this has been virtually eliminated in developed countries, it is still common where the quality of living is not as high.

In the course of the last decade many companies have been successful in creating catheter or minimally invasive implantable aortic valves, but such implantation of a mitral valve is more difficult. Patients would be benefited by implanting a device by a minimally invasive surgical procedure employing a small incision or by a catheter implantation such as from the groin. From the patient's point of view, the catheter procedure is very attractive. Many patients who require mitral valve replacement are elderly and an open heart procedure is painful, risky and takes time for recovery. Some patients are not even candidates for such a surgery due to their advanced age and frailty.

SUMMARY

Previous filings (for example, International PCT Publication No. WO 2013/114214, the disclosure of which is hereby incorporated by reference herein) have provided a disclosure on the use of an anchor to attach a mitral valve prosthesis in a patient via a catheter or minimally invasive procedure. The anchor most commonly described in these disclosures is a helical anchor which is first placed near the native mitral valve annulus and then the prosthetic valve is implanted inside the anchor. It would also be possible to add a helical anchor after the prosthetic valve was placed. The helical anchor can be placed to improve the stability of the prosthesis, to prevent rocking or even to control a leak that occurs around the valve. Whether the anchor is placed before or after the valve implant, this creates a two-step procedure for the interventionalist. He or she must first place the anchor, and then place the prosthetic valve, or vice versa.

It would be useful to have devices and methods to combine the anchor delivery with the valve delivery to simplify the procedure. A single surgical procedure can also reduce the impact on the patient.

Embodiments of the present invention include a delivery device and system for delivering a prosthetic mitral valve and an anchoring device, such as a helical anchoring device, and methods thereof. The prosthetic mitral valve and the helical anchoring device can be contained within a catheter that delivers both the prosthetic mitral valve and the helical anchoring device to a mitral position of a patient in a single procedure.

According to an embodiment of the invention, a mitral valve prosthesis includes an expandable valve frame and a plurality of arms each connected to the valve frame at or near a first end of the valve frame. A first arm from among the plurality of arms has a shape that is different from a shape of each of the other arms. The first arm is configured to guide a helical anchoring device around the valve frame.

According to another embodiment, a mitral valve prosthesis includes an expandable valve frame, a first arm having a first end attached to the valve frame and a second end configured to extend farther radially from a central axis of the valve frame than the valve frame extends from the central axis when the valve frame is in an expanded configuration, and an anchoring device including a coil that defines an inner space. The valve frame is held by the anchoring device when the valve frame is in the expanded configuration in the inner space of the coil.

According to another embodiment, a method for delivering a mitral valve prosthesis to a native mitral valve of a heart includes positioning a catheter at the native mitral valve, advancing an arm and a first end of a valve frame out of the catheter to a left ventricle of the heart, advancing an anchoring device out of the catheter into the left ventricle around leaflets and chordae tendineae of the native mitral valve, wherein the anchoring device is guided by at least a portion of the arm during the advancing of the anchoring device, and advancing remaining portions of the valve frame out of the catheter, wherein the valve frame is expanded and held in an inner space defined by a coil of the anchoring device.

BRIEF DESCRIPTION OF THE DRAWINGS

Further features and advantages will become apparent from the description of embodiments using the accompanying drawings. In the drawings:

FIGS. 4A-4B show close-up perspective views of the end of a valve delivery catheter and an adjacent helical anchor delivery catheter from which a prosthetic mitral valve and a helical anchoring device are respectively delivered, according to a further embodiment.

FIG. 4C shows a close-up perspective view of the helical anchoring device and the prosthetic valve of FIGS. 4A-4B after delivery from the adjacent helical anchor delivery catheter and the valve delivery catheter, respectively.

DETAILED DESCRIPTION

Disclosed herein are prosthetic mitral heart valves and anchors for use with such valves that allow for a simplified and improved implantation. In various embodiments, a helical anchoring device is formed as a coiled or twisted anchor that includes one or more turns that twist or curve around a central axis. The prosthetic mitral valve is expanded and held within the coil. The anchor and the valve can be delivered in a single procedure. By combining anchor placement with valve implantation, the patient benefits from a faster and simpler prosthetic valve implantation process.

Figure 1A:
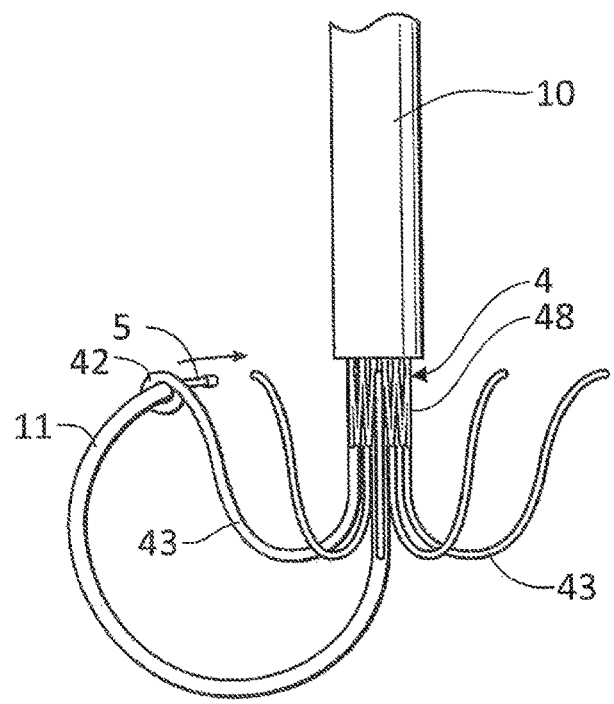
FIGS. 1A-1B show close-up perspective views of an end of a delivery catheter from which a prosthetic valve and a helical anchoring device are being delivered, according to a first embodiment of the invention.
Figure 1B:
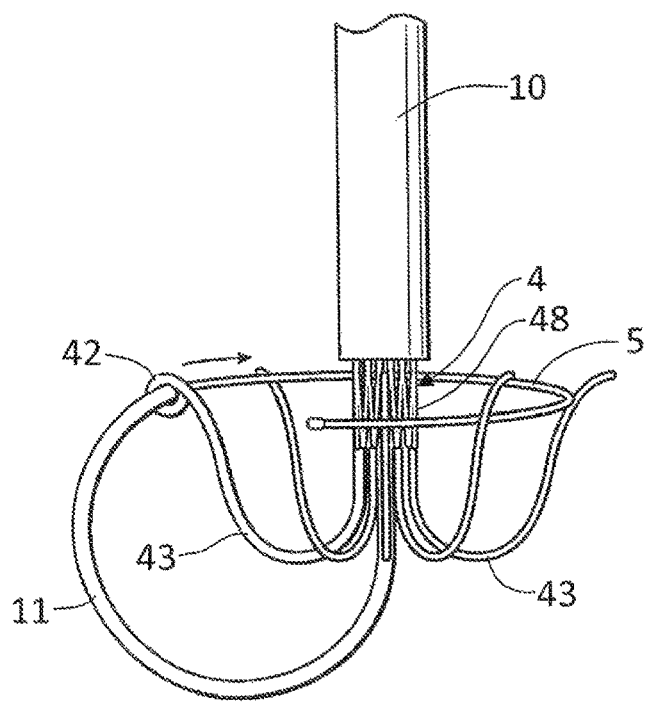

FIGS. 1A-1B show close-up perspective views of an end of a delivery catheter 10 from which a prosthetic valve 4 and a helical anchoring device 5 are being delivered, according to a first embodiment of the invention. For clarity, structures of the heart have been omitted in these figures.

FIG. 1A shows the prosthetic valve 4 with a portion extending from the delivery catheter 10, and a portion that is still being held in the delivery catheter 10. The prosthetic valve 4 includes a valve frame 48 that is expandable from a collapsed position or configuration in which a diameter of the valve frame 48 is reduced to an expanded position or configuration in which the diameter of the valve frame 48 is increased. The valve frame 48 can be collapsed to facilitate delivery through the delivery catheter 10, and can be expanded during or after placement at a native mitral valve, in order to engage the mitral valve annulus or an anchoring device 5 placed at the mitral position, as will be discussed in greater detail below. The valve frame 48 further houses a plurality of leaflets 41 (e.g., as shown in FIG. 2F) for regulating or controlling blood flow through the prosthetic valve 4.

The prosthetic valve further includes a plurality of arms 43 that are attached to the valve and extend from the valve frame 48. The arms 43 can be attached to a distal end of the valve frame 48, so that the arms 43 begin exiting the catheter 10 prior to the valve frame 48 during delivery of the prosthetic valve 4. Alternatively, the arms 43 can be attached higher up towards a center the valve frame 48, away from the distal end (e.g., as seen in FIG. 2F). The arms 43 are curved, with a first portion that extends distally away from the end of the valve frame 48, and a second portion that curves back up towards the valve frame 48 and extends radially outwardly of the valve frame 48. The second portion of the arms 43 will generally extend radially outwardly farther than the valve frame 48 even after the valve frame 48 has been expanded. The arms 43 are shaped in this manner to facilitate positioning around the native mitral valve leaflets.

At least one of the arms 43 is arranged differently (e.g., having a different shape) than the other arms 43. FIG. 1A shows a loop 42 at a distal end of the leftmost illustrated arm 43. The loop 42 is formed by further bending the end of the arm to define a circular opening. A size of the opening defined by the loop 42 is such that the helical anchoring device 5 can pass through and be guided through the loop 42. The loop 42 may also be slightly larger, in order to also hold and/or guide a helical anchor delivery catheter 11 through which the helical anchoring device 5 is deployed. The loop 42 allows the helical anchor delivery catheter 11 to swivel and to be adjusted into a desired delivery position.

The helical anchor delivery catheter 11 is used to deploy and position the helical anchoring device 5. The helical anchor delivery catheter 11 can initially be threaded through or held in the loop 42 of the prosthetic valve 4 during delivery of the prosthetic valve 4 through the catheter 10. In this manner, the deployment of the arms 43 will naturally also bend and/or otherwise position the helical anchor delivery catheter 11 into or close to the desired position for delivery of the helical anchoring device 5. In other embodiments, the helical anchor delivery catheter can alternatively be guided to and through the loop 42 after the respective parts have been delivered from the catheter 10. In the embodiment shown in FIGS. 1A and 1B, the helical anchor delivery catheter 11 is positioned in and passes through the prosthetic valve 4 in the catheter 10. However, in other embodiments, the helical anchor delivery catheter 11 can instead be positioned beside the prosthetic valve 4 (i.e., parallel to prosthetic valve 4) in the catheter 10, or for example can be positioned entirely outside of the catheter 10, as shown in and as will be later discussed with respect to FIGS. 4A-4B.

In some embodiments, the helical anchor delivery catheter 11 can have a preformed shape that facilitates the positioning of the helical anchor delivery catheter 11 once delivered from the delivery catheter 10. In some embodiments, the helical anchor delivery catheter 11 can be steerable through one of various means.

FIGS. 1A and 1B show an initial process of the helical anchoring device 5 being pushed out or otherwise delivered from the helical anchor delivery catheter 11. As will be discussed in greater detail below, the helical anchoring device 5 is formed as a coiled or twisted anchor that includes one or more turns that twist or curve around a central axis. The helical anchoring device 5 defines a generally circular or cylindrical inner space in which the valve frame 48 of the prosthetic valve 4 can expand and be held. The helical anchoring device 5 can be preformed to have the coiled or twisted shape, and is made of or includes a material that allows the helical anchoring device 5 to be deformed (e.g., straightened) when it is held in the helical anchor delivery catheter 11, and where the anchoring device 5 reverts back to its coiled shape when the anchoring device 5 is delivered from the helical anchor delivery catheter 11. The size and/or radius of curvature of the helical anchoring device 5, and the positioning of the helical anchoring delivery catheter 11, is such that the anchoring device 5 can be guided entirely around the native mitral valve leaflets and chordae tendineae when the anchoring device 5 is being deployed. FIG. 1A shows the beginning stages of deployment of the anchoring device 5, where only a distal tip of the anchoring device 5 extends from the helical anchoring delivery catheter 11, while FIG. 1B shows the anchoring device 5 being deployed almost one complete revolution around the valve frame 48 of the prosthetic valve 4. Implantation of the both the prosthetic valve 4 and the anchoring device 5 with respect to the various features of the heart will be discussed in greater detail with respect to FIGS. 2A-2F below.

FIGS. 2A-2F show a delivery system 100 and a method for positioning the prosthetic mitral valve 4 and the helical anchoring device 5 at the native mitral valve 3 of a patient's heart 2 according to the first embodiment.

Figure 2A:
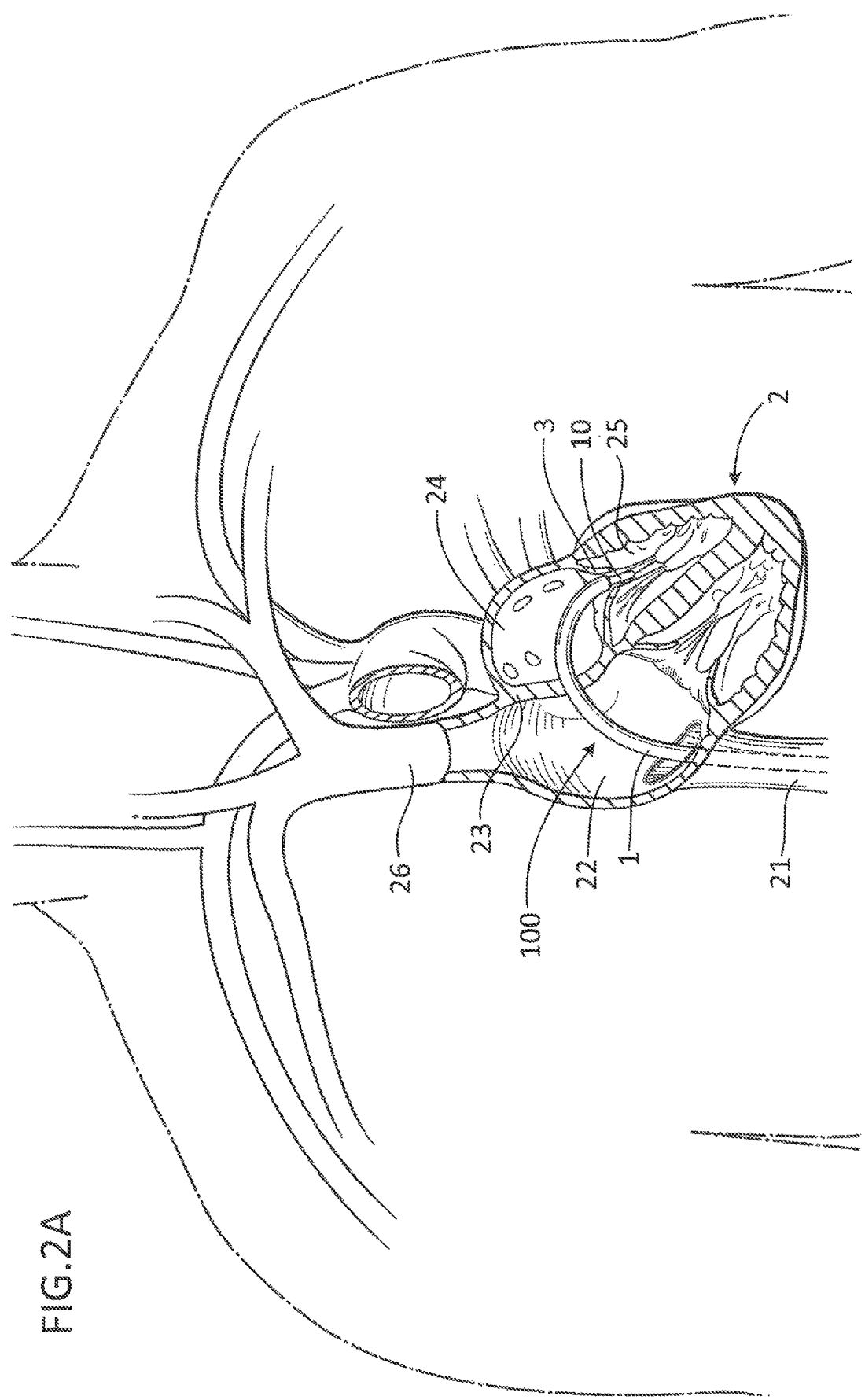
FIGS. 2A-2F are partial cross-sectional schematic views illustrating a process of employing a delivery system to implant the helical anchoring device and the prosthetic mitral valve in the mitral position of a heart, according to the first embodiment.
Figure 2B:
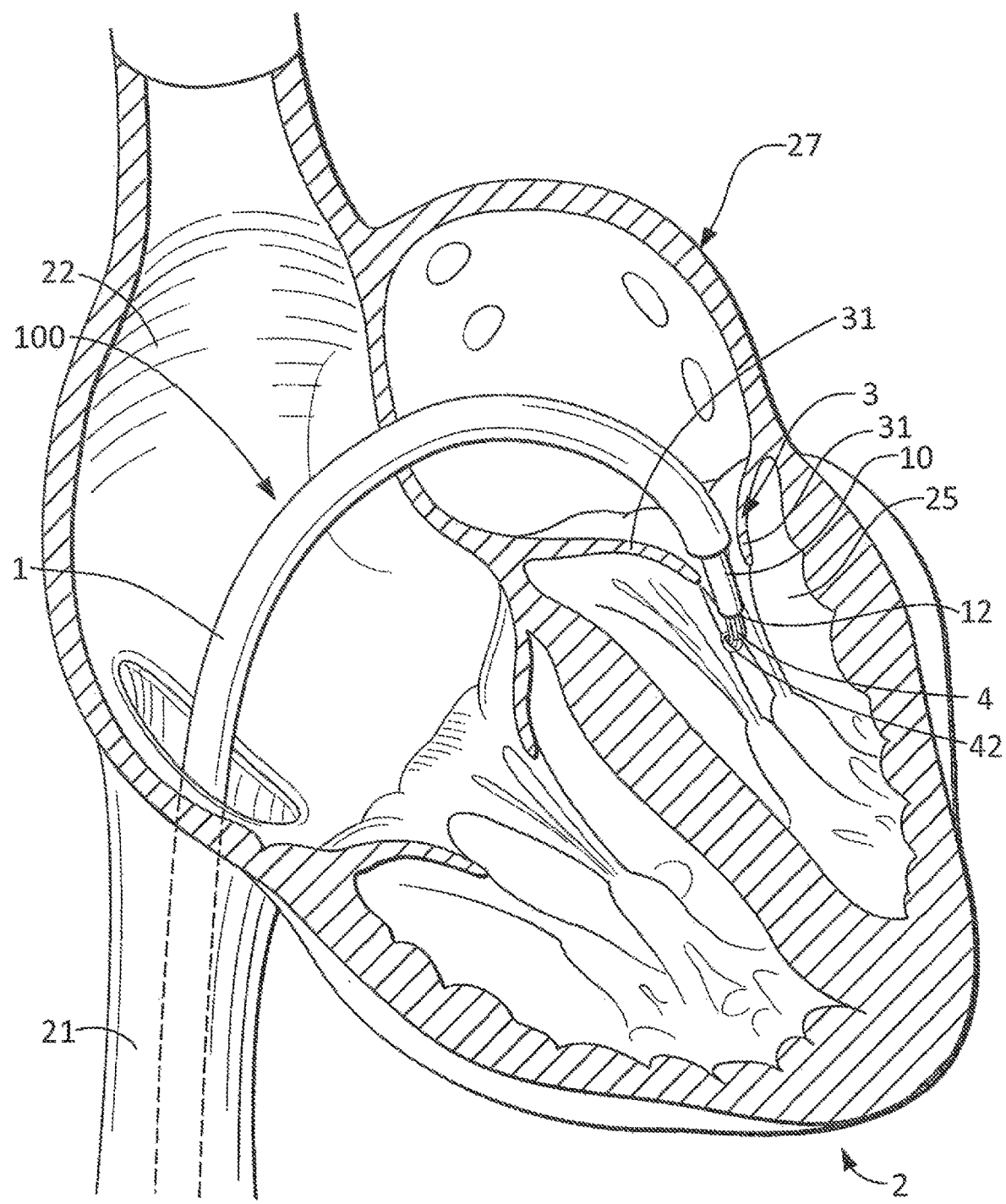
Figure 2C:
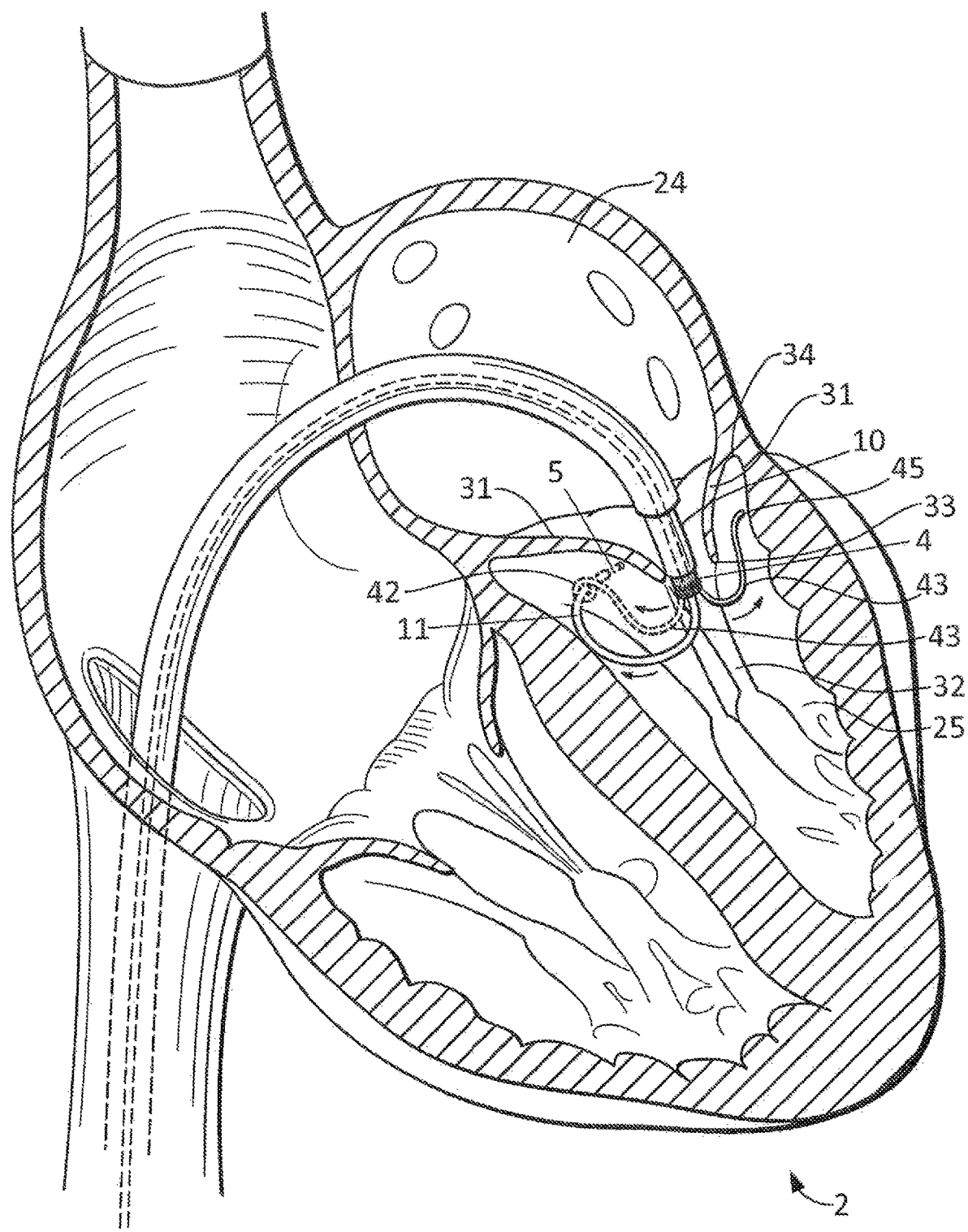
Figure 2D:
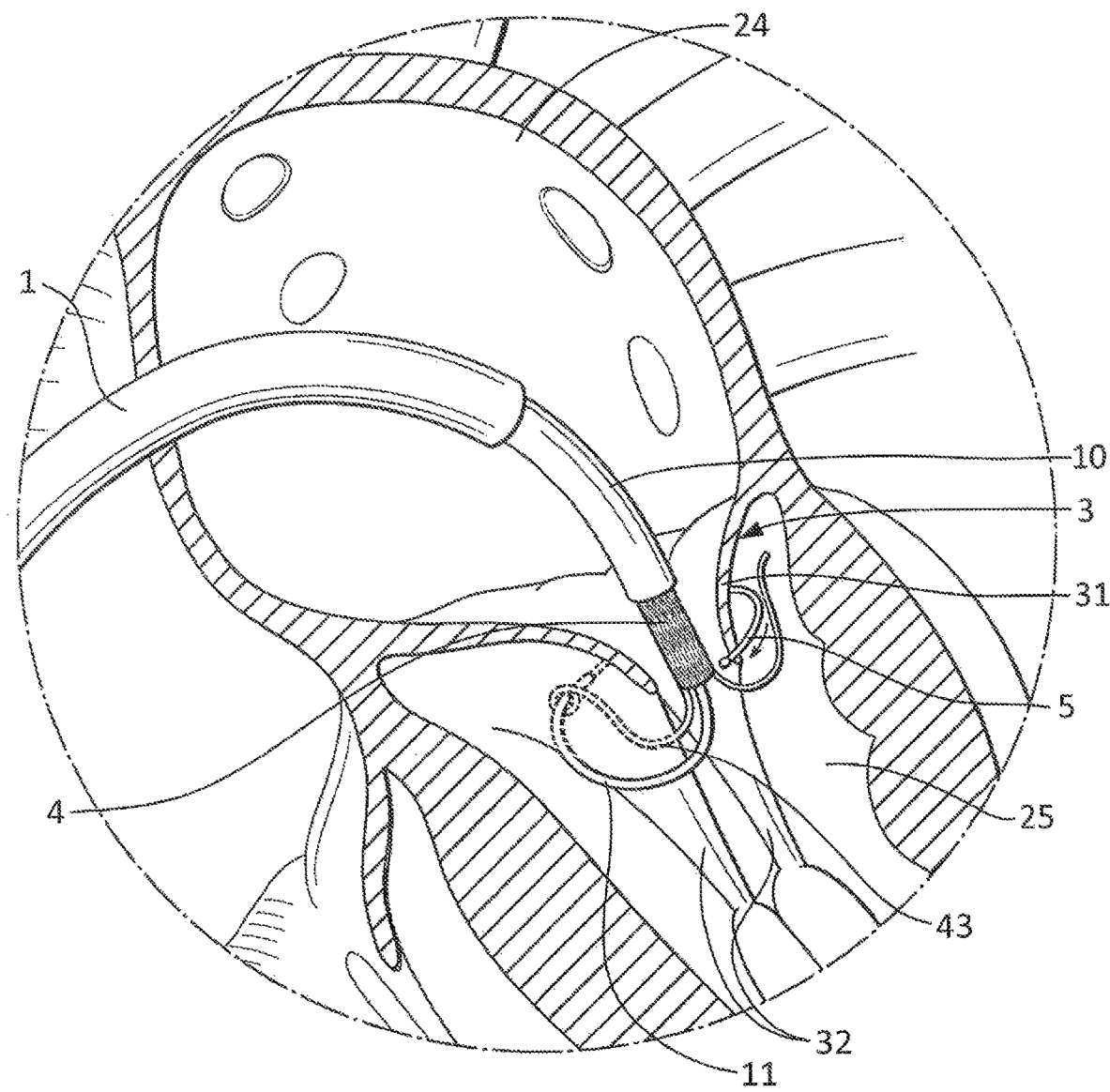

FIG. 2A shows the delivery system 100 including a catheter 1 which has been advanced in the heart 2 through a peripheral vein, for example, the inferior vena cava 21, into the right atrium 22, across the atrial septum 23 to the left atrium 24 and through the native mitral valve 3 such that the end of the catheter 1 sits in the left ventricle 25 near the native mitral valve 3. The catheter 1 can be introduced into a patient's venous system by percutaneous puncture or by a small surgical cut down at the patient's groin, as is commonly known. Alternatively, the catheter 1 can be introduced anywhere in the lower abdomen or retroperitoneal region, or in the neck or shoulder regions through the subclavian or axillary veins or the jugular system in the neck. In further embodiments, the catheter 1 can be introduced through the superior vena cava 26 or can enter the heart 2 directly through an outer wall of the left atrium 24. As shown in FIG. 2A, the delivery catheter 10 extends from the catheter 1 and is positioned in the left ventricle 25.

Figure 2E:
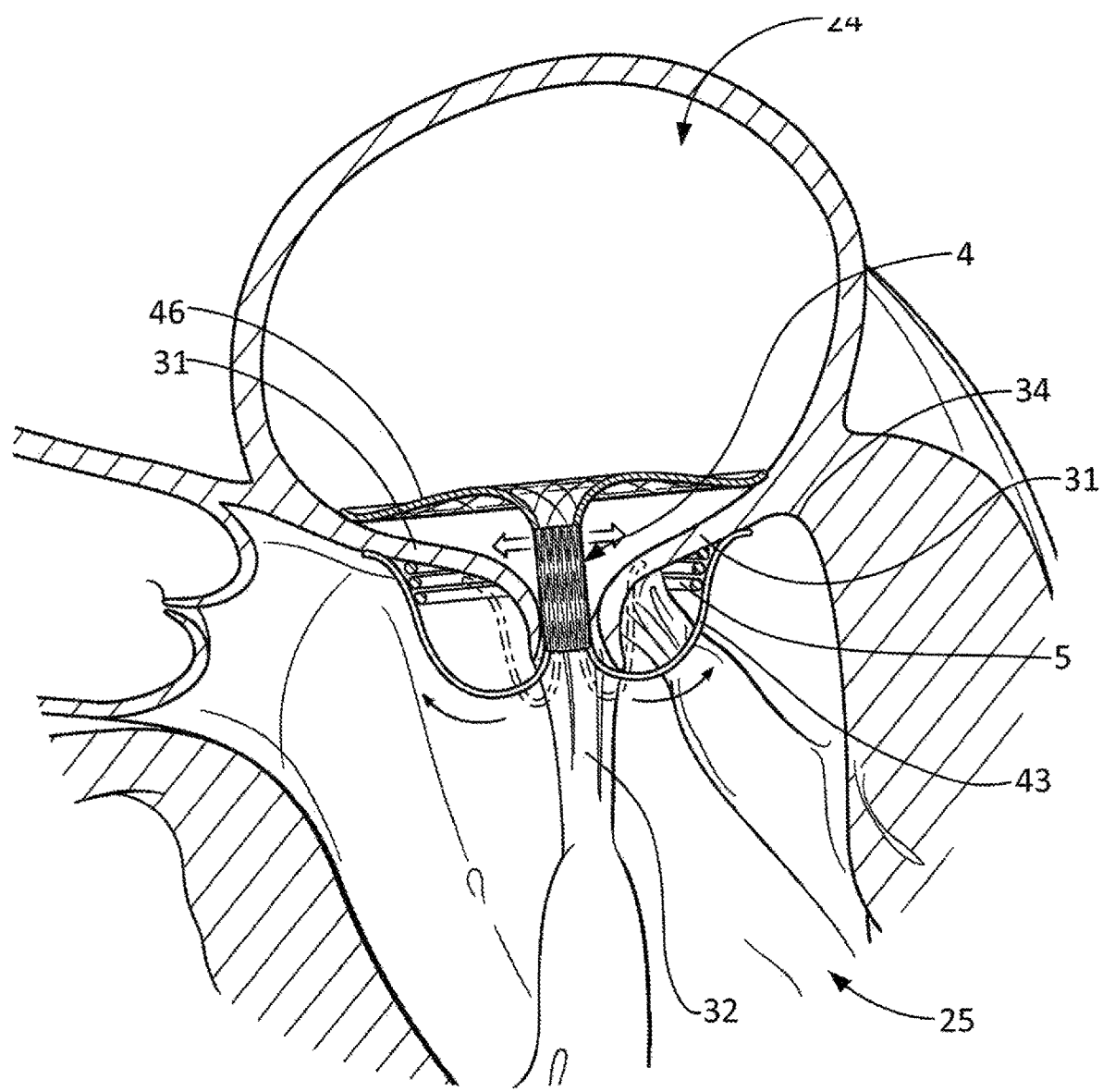
Figure 2F:
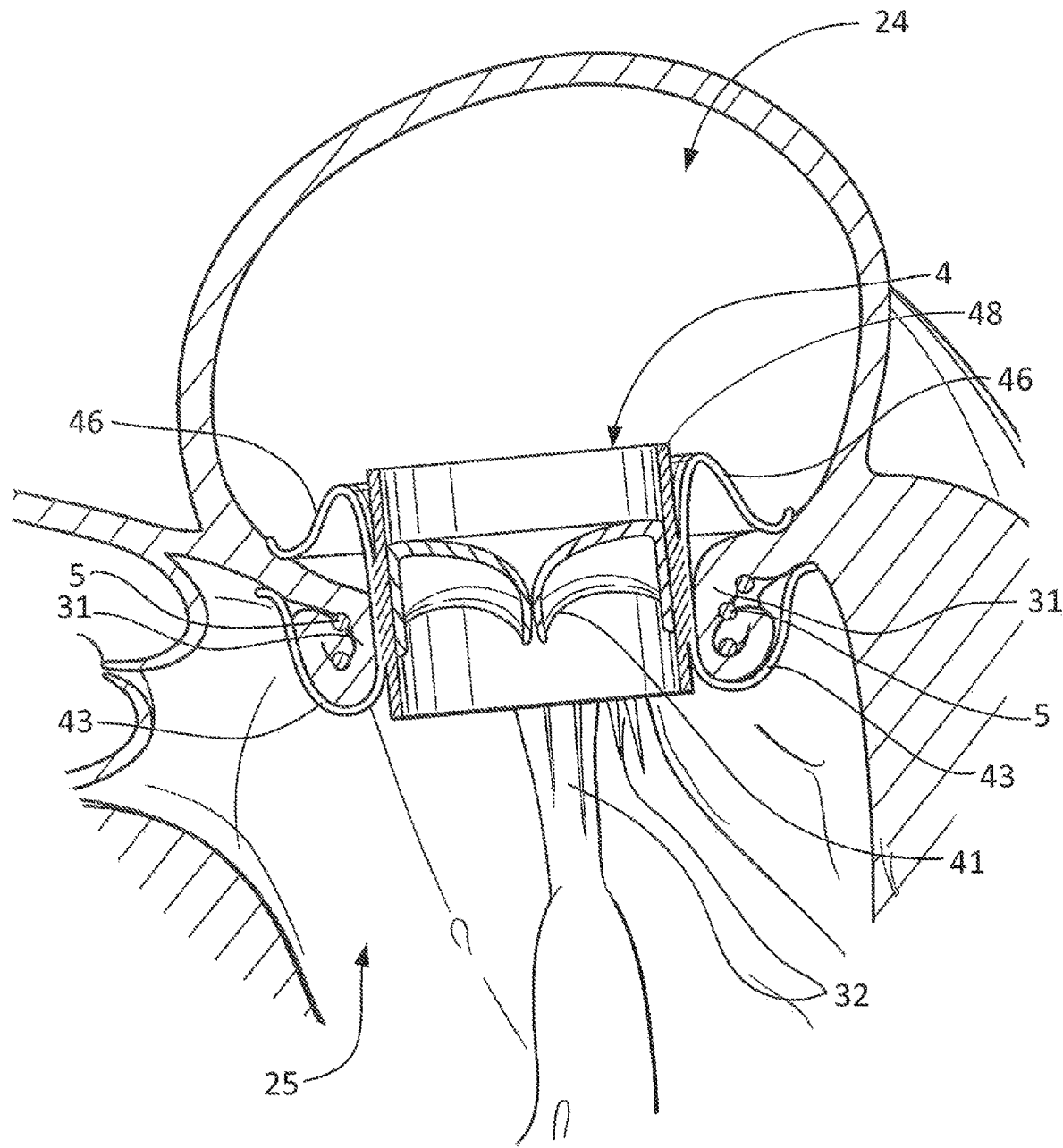

The catheter 10 contains or holds the prosthetic mitral valve 4 that can be implanted in the region of the patient's native mitral valve 3, as shown in FIGS. 2E-2F. The prosthetic valve 4 is expandable as previously discussed, and can be self-expanding. Nitinol is typically used to create the valve frame 48 of the self-expanding prosthetic valve 4, but other shape memory materials can be used as well. The valve frame houses artificial leaflets 41, as shown in FIG. 2F, which are typically made from cow or pig pericardium. The leaflets 41 can also be synthetic or derived from other sources such as human cadavers or by biologic tissue engineering. One biologic material which has favorable properties is tissue derived from small intestinal mucosa.

FIG. 2B shows a close up view of the catheter 1 located inside the left heart 27 with the tip 12 of the delivery catheter 10 just below the native leaflets 31 of the mitral valve 3. A portion of the prosthetic valve 4 has been delivered (e.g., deployed outwardly) from the delivery catheter 10 within the left ventricle 25 such that the loop 42 protrudes from the tip 12 of the delivery catheter 10.

FIG. 2C shows the further delivery of the prosthetic mitral valve 4 from the delivery catheter 10. The arms 43 extend from or near the end of the valve frame 48 of the prosthetic valve 4 that sits in the left ventricle 25, and wrap around the native leaflets 31 and serve to anchor the prosthetic valve 4 firmly against the margins of the native mitral leaflets 31. The arrows illustrate the direction in which the arms 43 wrap around the lower margin of the native mitral leaflets 31 after the arms 43 have been outwardly deployed from the delivery catheter 10. The arms 43 will help prevent the prosthetic valve 4 from dislodging upward into the left atrium 24 when the prosthetic valve 4 is fully positioned.

A number of arms 43 are useful to provide a lower plane of attachment of the prosthetic mitral valve 4 to the native mitral valve 3. The arms 43 can vary in length and in character and construction. It will be understood that more or less than two arms 43 can be used with this embodiment, even though only two arms are shown in FIGS. 2A-2F for the purposes of illustration.

One of the arms 43 has the loop 42 at its far or distal end to direct or control a helical anchor delivery catheter 11 that contains the helical anchoring device 5. In this embodiment, the helical anchor delivery catheter 11 has been preloaded into the loop 42. The arm 43 including the loop 42 can be of heavier construction than the other arms 43 and does not have to resemble the other arm or arms 43 that do not include a loop 42.

The arms 43 have shape memory properties or are otherwise resilient, such that when they are deployed outwardly from the delivery catheter 10 they can revert back to their curved shapes and wrap around the native mitral leaflets 31.

The arm 43 with the loop 42 wraps around the native mitral leaflet 31 and the attached helical anchor delivery catheter 11 is carried with it so that the chordae tendineae 32 and the patient's mitral valve leaflets 31 sit inside (i.e., on a concave side of the curvature of) an exposed end of the helical anchoring device 5. When the helical anchoring device 5 is advanced from this location, it will encircle the chordae tendineae 32 so that the native mitral valve leaflets 31 and the chordae 32 will be trapped inside a circle created by the helical anchoring device 5, as will be seen later.

The loop 42 at the end of the arm 43 swings the helical anchor delivery catheter 11 around the leaflets 31 and above the chordae 32 into a preferred position under the native mitral valve annulus 34. This particular arm 43 can have a double function of attaching the prosthetic valve 4 to the leaflet margin and guiding delivery of the helical anchoring device 5. The loop 42 can be sufficiently large to allow the helical anchor delivery catheter 11 to pivot or swivel as the system is deployed.

The helical anchoring device 5 is preferably delivered in a plane close to parallel to the underside of the native mitral valve 3. The helical anchor delivery catheter 11 is also aimed or directed to this plane by the loop 42. In one embodiment, the loop 42 can include a short tube that forces the helical anchor delivery catheter 11 into a favorable plane and orientation. Or the helical anchor delivery catheter 11 can be steerable. Many steerable catheters are known and available in the field of art.

In further embodiments, devices other than the loop 42 can direct the delivery of the helical anchoring device 5. For example, a cell of a stent frame that composes part of the prosthetic mitral valve 4 can also perform the same function as the loop 42 shown here. A hook or a tube can also be used. Any structure that can direct the helical anchoring device 5 around the native leaflets 31 can be added to the prosthetic valve 4. The structure can be permanently fabricated in the prosthetic valve 4 or can be temporary. For example, a loop of suture could be used to create the loop 42. The suture could then be withdrawn. In other embodiments, prior mitral valve prosthetics having arms or wings can be modified or retrofitted with the loop 42 of the present prosthetic valve 4 in order to facilitate delivery of the helical anchoring device 5.

The arms 43 in FIGS. 2C-2F can be quite slender. In practice, the arms 43 can be composed of pairs or triplets of wires that are fused at the ends 45 of the arms 43. These narrow terminal ends 45 to the arms 43 facilitate the arms 43 passing between the chordae tendineae 32 at their margin with the free edges 33 of the mitral leaflets 31 to allow the arms 43 to wrap around the leaflets 31. The chordae 32 are closely packed around some areas of the native mitral valve 3, and slender arms 43 will better facilitate passing of the arms 43 between the chordae tendineae 32. Once the slender part of the arms 43 pass, thicker parts of the arms 43 can move between the chordae 32 by spreading them apart. Thus, in some embodiments, the arm 43 is slender (or composed of a single wire or a fusion of wires) at the tip 45 and is more robust closer to the main body of the prosthetic valve 4 (for more powerful attachment). Further, the arms 43 can also be shorter or longer than illustrated in FIGS. 2C-2F.

Deployment of the helical anchoring device 5 can be started anywhere around the mitral valve annulus 34. For example, deployment of the helical anchoring device 5 can start in or adjacent to the middle of a leaflet 31. This would be an advantage for an operator who, for example, would not have to precisely locate a commissure of the native mitral valve to begin the anchoring device delivery procedure, thereby simplifying the procedure.

FIG. 2D shows a close-up schematic view of the helical anchoring device 5 being delivered under the native mitral valve leaflets 31 at the mitral position. The arrow illustrates the direction in which the helical anchoring device 5 is deployed from the delivery catheter 11 under the native mitral valve 3. Any number of turns can be delivered depending on the particular helical anchoring device 5 used. An inner diameter of the helical anchoring device 5 can preferentially be slightly less than an outer diameter of the fully expanded mitral prosthetic valve 4 in order to promote engagement between the helical anchoring device 5 and the prosthetic valve 4.

The partially delivered prosthetic valve 4 can serve to center the delivery of the helical anchoring device 5. It can also provide a stable platform for delivery of the helical anchoring device 5.

In the embodiment illustrated in FIG. 2E, three turns of the helical anchoring device 5 have been placed below the native mitral valve 3. The native mitral valve leaflets 31 are positioned between the helical anchoring device 5 and the prosthetic mitral valve 4, which is shown in FIG. 2E as being about to expand. Once the prosthetic valve 4 is expanded, the helical anchoring device 5 aids in securely positioning the prosthetic valve 4 and prevents leaks around the prosthetic valve 4 by sealing the native leaflets 31 to or against the prosthetic valve 4. Opposing forces between the helical anchoring device 5 and the prosthetic valve 4 help position and stabilize the prosthetic valve 4.

In FIG. 2E, the delivery catheter 10 has been omitted for simplicity. In practice, the prosthetic valve 4 would spring open in FIG. 2E when the delivery catheter 10 has been removed (the arrows indicate the direction in which the prosthetic valve 4 would normally spring open). However, in FIG. 2E the prosthetic valve 4 is still in a closed position in order to allow clear visualization of the turns of the helical anchoring device 5 under the native mitral valve 3. In this embodiment, the prosthetic valve 4 further includes an expandable atrial portion 46 that extends or projects from or near a second end of the valve frame 48 opposite the end from which the arms 43 extend. The atrial portion 46 is configured to be held against or to abut against a wall of the left atrium 24, to help further stabilize the prosthetic valve 4 at the mitral position. The atrial portion 46 of the prosthetic valve 4 can expand to a size greater than the mitral valve annulus 34, for example, to restrict movement of the prosthetic valve 4 into the left ventricle 25.

In the embodiment of FIG. 2E, there are three turns of the helical anchoring device 5, but any number of turns can be used. The turns sit up against the underside of the mitral valve annulus 34 and the leaflets 31 in order to provide a solid buttress to fix the helical anchoring device 5 in position and to prevent movement of the prosthetic valve 4 into the left atrium 24 when the left ventricle 25 contracts. Since the arms 43 are wrapped around the helical anchoring device 5, the entire structure is stabilized in position.

The use of a helical anchoring device that can optionally be delivered at the same time as a prosthetic valve provides the interventionalist a considerable amount of choice. For example, some embodiments of the prosthetic valve 4 are able to be re-sheathed, i.e., re-inserted into the delivery catheter 10, allowing the prosthetic valve 4 to be partly advanced and tested for its fit during a procedure. If the operator is not happy with the positioning before the final release of the prosthetic valve 4, the prosthetic valve 4 can be pulled back into the delivery catheter 10.

In some methods of use, the prosthetic valve 4 can be positioned first without the helical anchoring device 5 in place. If the anchoring of the prosthetic valve 4 appears to be strong and stable and there is no evidence of movement or leak, the prosthetic valve 4 can be released without the helical anchoring device 5. On the other hand, if the operator is not satisfied with, for example, the position or stability of the prosthetic valve 4 in the mitral position without the helical anchoring device 5, the prosthetic valve 4 can be pulled back into the delivery catheter 10. Then, the helical anchoring device 5 can be placed first and the prosthetic valve 4 can be positioned and expanded therein. This would let the user decide the clinical need for the extra anchoring of the helical anchoring device 5 based on each individual procedure.

In FIG. 2F, the fully implanted prosthetic valve 4 is shown in the mitral position. The arms 43 have wrapped around the native mitral valve leaflets 31 to prevent the prosthetic valve 4 from moving upward into the left atrium 24. The native mitral leaflets 31 are compressed tightly under the arms 43 and a solid mechanical structure has been created to prevent the prosthetic valve 4 from migrating.

The turns of the helical anchoring device 5 also compress against the body of the prosthetic valve 4 to position, orient and prevent movement of the prosthetic valve 4. The helical anchoring device 5 provides a frictional attachment of the body of the prosthetic valve 4 to the native mitral valve leaflets 31 and serves to anchor the arms 43 that wrap around the helical anchoring device 5.

The upper atrial portion 46 of the prosthetic mitral valve 4 is shown with a wide area that sits inside the left atrium 24 to promote attachment to or abutment against the wall of the left atrium 24. However the force or pressure that tends to urge the prosthetic mitral valve 4 from the left atrium 24 into the left ventricle 25 is low, and so the atrial portion 46 may not be necessary and could be eliminated or reduced in a clinical prosthesis according to some embodiments.

The turns of the helical anchoring device 5 aid in overcoming variations in the lengths of the patient's leaflets 31, variations in the length of the chordae tendineae 32 and variations in the attachment point of the chordae 32 in the left ventricle 25. When a prosthetic mitral valve with arms 43 wrapping around the leaflets 31 is used without any helix or anchor encircling under the leaflets 31, the depth or robustness of fixation of the prosthetic mitral valve can vary around the perimeter of the implanted prosthetic mitral valve. For example, if the chordae tendineae 32 attached to the middle part of the posterior leaflet 31 were very elongated or ruptured (a common situation), the arms 43 can fail to wrap around and engage the leaflet 31 at this location. Or there can be a very limited engagement between one of the arms 43 and the leaflet 31, causing the arm 43 to move to or come to rest at a much higher plane closer to the valve annulus 34. If any of these occurs, the part of the prosthetic valve where this happens would sit higher or closer to the native mitral valve 3, which may create a skew in the prosthetic valve so the prosthetic valve would sit at an angle to the plane of inflow of the valve. As the heart beats, there is a large load on the prosthetic valve and it can begin to rock and shift. The heart beats almost 100,000 times per day and after several days or weeks or months, the prosthetic valve may shift, move and dislodge. Also, if the leaflets 31 or chordae 32 were very elongated, there may be no contact with the arms, and an effective seal around the implant may not be formed. This could result in a large paravalvular leak due to lack of engagement of the prosthetic valve with the native mitral leaflets 31. The helical anchoring device 5 under the leaflets 31 can compress leaflet tissue against the prosthetic valve and prevent this problem. The helical anchoring device 5 can sit in one plane and prevent problems related to variations in patient anatomy.

In clinical practice, there are virtually limitless variations in the size of the leaflets 31, the character of the leaflets 31, the chordal lengths and the attachment of chordae 32 as well as the diameter of the mitral annulus 34. The use of the helical anchoring device 5 under the leaflets 31 neutralizes many of these variables since the fixation point of the arms 43 can be brought to the lowest turn of the helical anchoring device 5. This position can be determined in advance by selecting the number of turns of the helical anchoring device 5 and the thickness of the helical anchoring device 5 to match the turning point of the arms 43 at the lowest part of the prosthetic valve 4.

Thus, the helical anchoring device 5 can create a common and predefined plane for the anchoring of the arms 43 of the prosthetic mitral valve 4. In the situation described previously where some of the chordae 32 are stretched and where contact between the prosthetic valve 4 may otherwise be loose or less secure without the helical anchoring device 5, the attachment of the prosthetic mitral valve 4 in this region can be to the helical anchoring device 5 instead. This would create a common plane for the lowest point of the prosthetic mitral valve 4.

Therefore, more turns of the helical anchoring device 5 can be added to ensure the arms 43 of the prosthetic valve 4 are at a common lowest plane throughout its perimeter. In some embodiments, the helical anchoring device 5 can be made thicker. In some embodiments, waves or undulations can be added to the turns of the helical anchoring device 5 to expand the height of the helical anchoring device 5.

The helical anchoring device 5 thus improves stability of the prosthetic valve 4 by providing an anchor point for the arms 43 of the prosthetic valve 4 to wrap around and at the same time the helical anchoring device 5 can trap the perimeter of the barrel of the prosthetic valve 4 along its length. The combination of these features provides great stability to the prosthetic valve 4. It also seals the native mitral valve 3 against the prosthetic valve 4 to prevent a paravalvular leak.

In addition, patients' native mitral valves (i.e., leaflets 31, annulus 34, and chordae 32) come in all varieties and combinations. It is less practical for a manufacturer to make different lengths and depths of anchoring arms 31 and for the operator to deliver these products perfectly into position inside the patient. It can be more practical to adjust for these variations by placing the helical anchoring device 5 below the prosthetic valve 4 and using this helical anchoring device 5 to create a lowest plane for the arms 43 to anchor against.

Figure 3A:
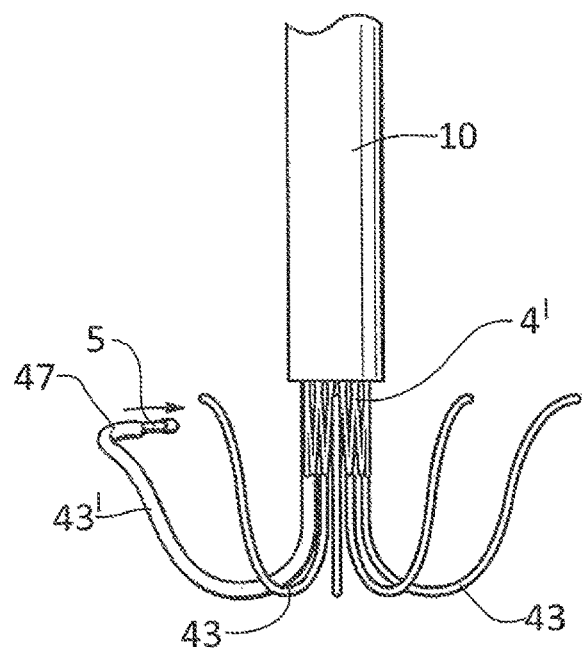
FIGS. 3A-3B show close-up perspective views of the end of the delivery catheter from which a prosthetic mitral valve with a modified arm is being delivered, according to a second embodiment.
Figure 3B:
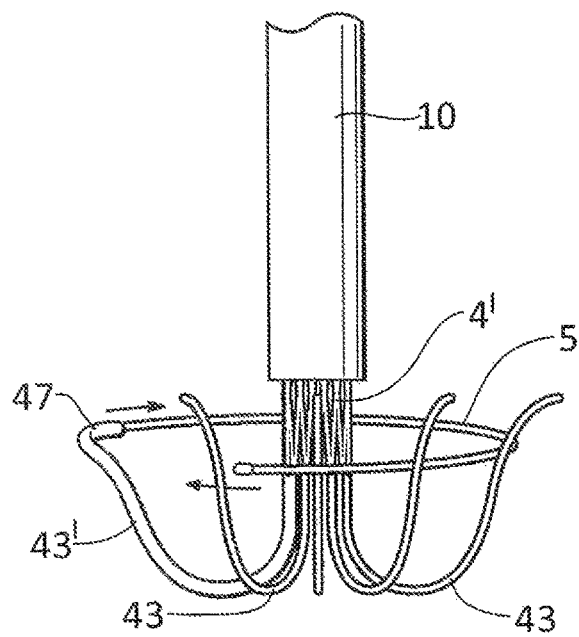

FIGS. 3A-3B show the end of the delivery catheter 10 from which a prosthetic valve 4' is being delivered, according to a second embodiment. For clarity, structures of the heart 2 have been omitted in these figures.

In the embodiments described above, the helical anchor delivery catheter 11 that delivers the helical anchoring device 5 under the native mitral leaflets 31 is separate from the prosthetic device 4. In the embodiment illustrated in FIGS. 3A-3B, the helical anchor delivery catheter has been incorporated into the prosthetic valve 4' as a modified arm 43'. The prosthetic valve 4' includes the modified arm 43' that wraps around one of the mitral leaflets 31, similar to the other arms 43. Here, the modified arm 43' is a hollow tube that can be loaded with the helical anchoring device 5, and which is sized so that the helical anchoring device can be advanced therethrough. The modified arm 43' includes a bend 47 and a portion at a distal end that is angled relative to the rest of the arm 43', so that a distal portion of the arm 43' extends circumferentially around the prosthetic valve 4'. An opening of the hollow tube therefore points circumferentially around the prosthetic valve 4' to help direct the helical anchoring device 5 around the native mitral leaflets 31 and the chordae 32. However, any structure on the modified arm 43' of the prosthetic valve 4' or any part of the prosthetic valve 4' that could guide the helical anchoring device 5 can suffice to direct the helical anchoring device 5 into the correct position. When the modified arm 43' wraps around one of the mitral leaflets 31, the helical anchoring device 5 is carried into the correct location and to the correct plane for delivery. The modified arm 43' can be preformed and made of a shape-memory material, such as nitinol.

FIG. 3B shows almost one complete turn of the helical anchoring device 5 extending from the tubular arm 43'. As described above, the helical anchoring device 5 can complete multiple turns under or around the native mitral leaflets 31. As shown in this embodiment, the prosthetic mitral valve can be modified to carry the helical anchoring device 5 without the need for a separate helical anchor delivery catheter positioned under or around the native mitral leaflets 31.

FIGS. 4A-4B show close-up perspective views of the end of the delivery catheter 10 and an adjacent helical anchor delivery catheter 11".

In the embodiment shown in FIGS. 1A-1B, the helical anchor delivery catheter 11 is positioned inside the prosthetic mitral valve 4 in the catheter 10. However, in this embodiment, the helical anchor delivery catheter 11" and the prosthetic valve 4" are delivered side by side. As shown in FIGS. 4A-4B, the prosthetic valve 4 can be constructed similarly to the prosthetic valve 4 in the embodiment of FIGS. 1A-1B. The helical anchor delivery catheter 11" is instead positioned outside the delivery catheter 10 that delivers the prosthetic mitral valve 4". The helical anchor delivery catheter 11" passes through the loop 42 in one of the arms 43 in the prosthetic mitral valve 4". The arrows adjacent the helical anchoring device 5 demonstrate the direction in which the helical anchoring device 5 is being delivered from the end of the helical delivery catheter 11".

FIG. 4B shows the helical anchoring device 5 further extended from the helical anchor delivery catheter 11". The end of the helical anchor delivery catheter 11" is still in the loop 42 at the end one of the arms 43, and almost one full turn of the helical anchoring device 5 has been delivered.

FIG. 4C shows a close-up perspective view of the helical anchoring device 5 and the prosthetic valve 4" of FIGS. 4A-4B after delivery from the helical anchor delivery catheter 11" and the delivery catheter 10, respectively.

In FIG. 4C, about three turns of the helical anchoring device 5 have been delivered under the schematically illustrated plane 35 of the native mitral valve 3. However, any number of turns of the helical anchoring device 5 can be provided in order to provide support to the prosthetic valve 4". The helical anchor delivery catheter 11" has been removed in FIG. 4C for simplicity. The delivery catheter 10 delivering the prosthetic valve 4" has also been removed. As discussed regarding FIG. 2E above, the body of the prosthetic valve 4" would generally spring open when the delivery catheter 10 is removed. But for the purpose of illustration, the prosthetic valve 4" is shown in FIG. 4C in its closed position to make visualization of the helical anchoring device 5 and the prosthetic valve 4" clearer.

Various other modifications or alternative configurations can be made to the prosthetic valves, helical anchors, and/or deployment systems according to the above described embodiments of the invention. For example, any variation of the valve prosthesis where controlled deployment of a helical anchor can be facilitated by a portion of the prosthesis that interacts with either the helical anchor itself or with a catheter for delivering the helical anchor may be alternatively arranged. The interacting feature may be embodied in an arm of the valve prosthesis as described in some of the above embodiments, or may be a feature that is arranged on another portion of the valve prosthesis. With respect to the helical anchor, the number of coils can be further varied, based on for example, properties of the native mitral valve and/or desired positioning of the valve prosthesis. Various other coil shapes, lengths, and arrangements and modifications can also be made based on a wide range of considerations.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

In view of the many possible embodiments to which the principles of the disclosure may be applied, it should be recognized that the illustrated embodiments are only preferred examples and should not be taken as limiting the scope of the disclosure. Rather, the scope of the disclosure is defined by the following claims.

What is claimed is:

1. A valve prosthesis configured to be implanted at a native valve of a heart, comprising:
   an expandable prosthetic valve frame;
   a first arm connected to and extending from a first end of the valve frame;
   a second arm connected to and extending from the first end of the valve frame;
   wherein the entire first arm and the entire second arm are shaped differently from one another; and
   an anchoring device comprising a coil configured to define an inner space for receiving the valve frame, wherein only one of the first arm or the second arm is configured to deploy and guide the anchoring device around the valve frame.

2. The valve prosthesis of claim 1, wherein the first arm differs from the second arm in that the first arm comprises a closed annulus that defines an opening through which an anchoring device is guided.

3. The valve prosthesis of claim 1, wherein the first arm differs from the second arm in that the first arm comprises a hollow tube through which an anchoring device is guided.

4. The valve prosthesis of claim 1, wherein the first arm is of a heavier construction than the second arm.

5. The valve prosthesis of claim 1, further comprising at least a third arm having a same shape as the second arm.

6. The valve prosthesis of claim 1, wherein the valve frame houses a plurality of prosthetic valve leaflets.

7. A valve prosthesis configured to be implanted at a native valve of a heart, comprising:
   an expandable prosthetic valve frame having a central axis;
   an arm connected to the valve frame; and
   an anchoring device comprising a coil configured to define an inner space for receiving the valve frame, wherein the arm is configured to deploy and guide the anchoring device around the valve frame;
   wherein when the valve prosthesis is implanted at a native valve, the anchoring device is configured to be detached from the arm, and the arm is configured to extend farther away radially from the central axis than the anchoring device extends from the central axis.

8. The valve prosthesis of claim 7, wherein a first portion of the arm extends axially away from a first end of the valve frame and a second portion of the arm extends axially from the first portion back towards the valve frame.

9. The valve prosthesis of claim 7, wherein the arm comprises a closed annulus that defines an opening through which an anchoring device is guided.

10. The valve prosthesis of claim 7, wherein the arm is a first arm, and wherein the valve prosthesis further comprises at least a second arm connected to the valve frame.

11. The valve prosthesis of claim 10, wherein the first arm is of a heavier construction than the second arm.

12. The valve prosthesis of claim 7, wherein the valve frame houses a plurality of prosthetic valve leaflets.

* * * * *